(12) United States Patent
Miyake (10) Patent No.: US 9,662,092 B2
(45) Date of Patent: May 30, 2017

(54) ULTRASOUND OBSERVATION APPARATUS (71) Applicant: OLYMPUS CORPORATION, Tokyo (JP)

(72) Inventor: Tatsuya Miyake, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/196,133

(22) Filed: Jun. 29, 2016

(65) Prior Publication Data

US 2016/0302768 A1 Oct. 20, 2016

Related U.S. Application Data (63) Continuation of application No. PCT/JP2015/076154, filed on Sep. 15, 2015.

(30) Foreign Application Priority Data

Oct. 6, 2014 (JP) ................................. 2014-205852

(51) Int. Cl.
*A61B 8/08* (2006.01)
*A61B 8/00* (2006.01)
*A61B 8/12* (2006.01)

(52) U.S. Cl.
CPC ................ *A61B 8/481* (2013.01); *A61B 8/12* (2013.01); *A61B 8/5215* (2013.01); *A61B 8/54* (2013.01)

(58) Field of Classification Search
CPC .. A61B 8/06; A61B 8/12; A61B 8/481; A61B 8/54
See application file for complete search history.

(56) References Cited

U.S. PATENT DOCUMENTS

| 2009/0030322 A1 | 1/2009 | Fujiwara et al. |
| 2011/0301457 A1 | 12/2011 | Yoshiara et al. |
| 2013/0182120 A1 | 7/2013 | Nakajima |

FOREIGN PATENT DOCUMENTS

| EP | 2394580 A1 | 12/2011 |
| JP | 2004-000739 A | 1/2004 |
| JP | 2004-202142 A | 7/2004 |
| JP | 4099437 B2 | 6/2008 |

(Continued)

OTHER PUBLICATIONS

International Search Report dated Dec. 8, 2015 issued in PCT/JP2015/076154.

*Primary Examiner* — Michael Rozanski
(74) *Attorney, Agent, or Firm* — Scully, Scott, Murphy & Presser, P.C.

(57) ABSTRACT

An ultrasound observation apparatus that generates an ultrasound image based on an ultrasound signal obtained by receiving ultrasound reflected by a contrast medium in a target region of a subject to which the contrast medium is administered includes a measuring section configured to measure predetermined measurement items related to administration of the contrast medium, an image quality setting changing section configured to change an image quality setting of the ultrasound image from one to another of a first image quality setting suitable for observing how the contrast medium flows into the target region and a second image quality setting suitable for observing how the contrast medium is retained in the target region, and a control section configured to control setting changing operation by the image quality setting changing section based on a measurement result of the measuring section.

14 Claims, 7 Drawing Sheets

(56) References Cited

FOREIGN PATENT DOCUMENTS

| | | |
|---|---|---|
| JP | 2009-028194 A | 2/2009 |
| JP | 2011-254963 A | 12/2011 |
| JP | 5632203 B2 | 11/2014 |
| WO | WO 2012/043312 A1 | 4/2012 |

ULTRASOUND OBSERVATION APPARATUS

CROSS REFERENCE TO RELATED APPLICATION

This application is a continuation application of PCT/JP2015/076154 filed on Sep. 15, 2015, and claims benefit of Japanese Application No. 2014-205852 filed in Japan on Oct. 6, 2014, the entire contents of which are incorporated herein by this reference.

BACKGROUND OF THE INVENTION

1. Field of the Invention

The present invention relates to an ultrasound observation apparatus that performs ultrasound observation using a contrast medium.

2. Description of the Related Art

In recent years, ultrasound observation apparatuses have been widely used which can acquire acoustic information on an interior of a subject in a non-invasive manner.

Furthermore, ultrasound observation techniques are also being developed which adopt a contrast imaging mode in which a contrast medium is injected or administered into a subject and movement of the bloodstream is imaged from ultrasound reflected by the contrast medium.

For example, Japanese Patent Application Laid-Open Publication No. 2011-254963 as a first conventional example discloses contents of an ultrasound observation apparatus that can perform observation using a contrast medium, configured to analyze a retention time period of the contrast medium from luminance information and display an ultrasound image classified using different colors in accordance with the analyzed retention time period to evaluate how the contrast medium is retained.

Furthermore, Japanese Patent Application Laid-Open Publication No. 2009-28194 as a second conventional example discloses an ultrasound observation apparatus that includes contrast medium inflow start detection means configured to detect inflow timing at which a contrast medium administrated to a subject starts flowing into an image pickup region using B mode image information of the image pickup region of the subject and post-processing starting means configured to start post-processing which is done after the contrast medium starts flowing into the image pickup region (target region) in synchronization with the inflow timing, in which the apparatus automatically detects the inflow of the contrast medium into the image pickup region and controls the starting of a timer or the like.

SUMMARY OF THE INVENTION

An ultrasound observation apparatus according to an aspect of the present invention is an ultrasound observation apparatus that transmits ultrasound to a subject to which a contrast medium is administered, receives the ultrasound reflected by the contrast medium in a target region of the subject and generates an ultrasound image based on an ultrasound signal obtained from the received ultrasound, the ultrasound observation apparatus including a measuring section configured to measure predetermined measuring items related to administration of the contrast medium, an image quality setting changing section configured to change an image quality setting of the ultrasound image from one to another of a first image quality setting suitable for observing how the contrast medium flows into the target region and a second image quality setting suitable for observing how the contrast medium is retained in the target region, and a control section configured to control setting changing operation by the image quality setting changing section based on a measurement result of the measuring section.

DETAILED DESCRIPTION OF THE PREFERRED EMBODIMENT

Hereinafter, an embodiment of the present invention will be described with reference to the accompanying drawings.

(First Embodiment)

Figure 1:
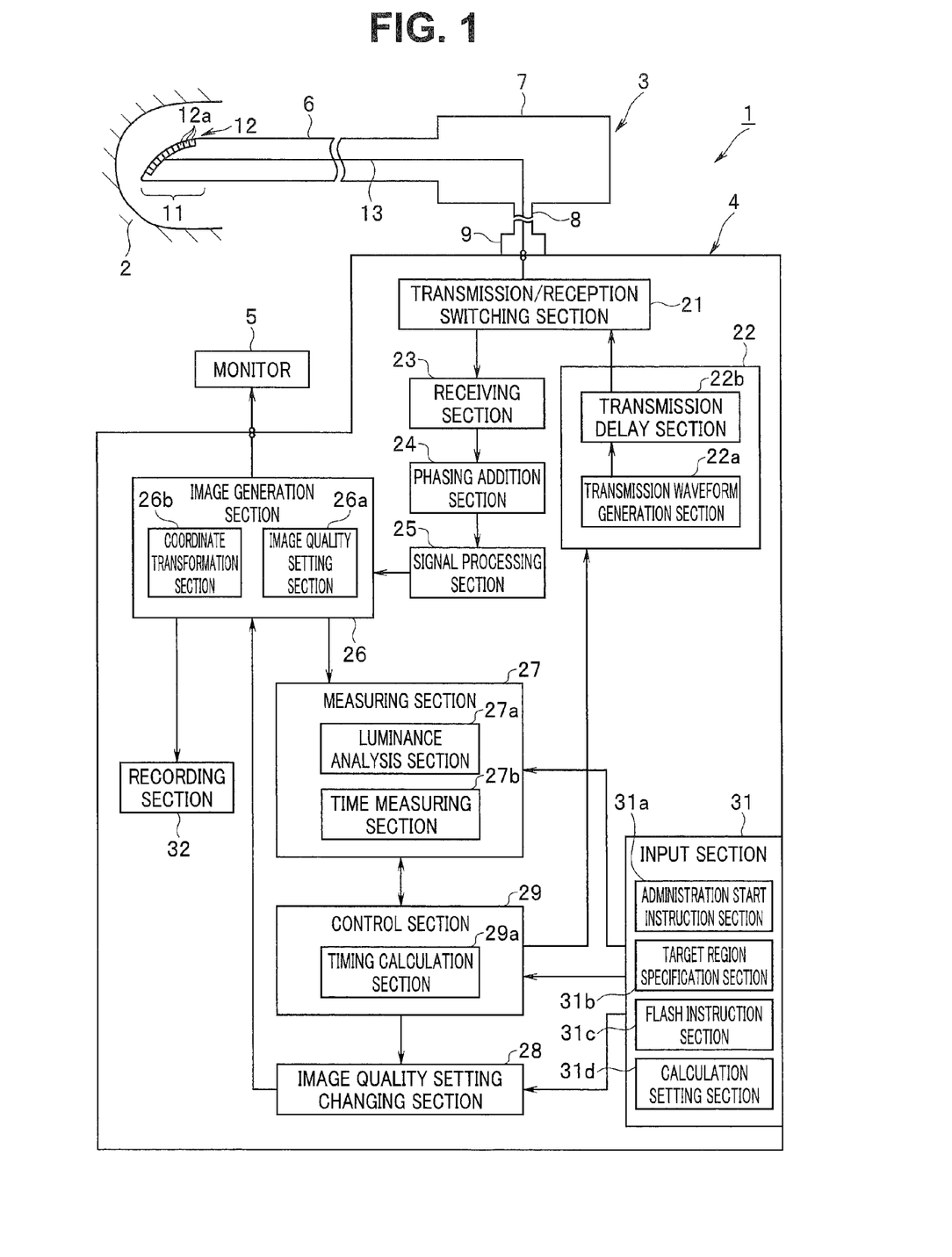
FIG. 1 is a diagram illustrating a configuration of an ultrasound diagnostic apparatus including an ultrasound observation apparatus according to a first embodiment of the present invention.

As shown in FIG. 1, an ultrasound diagnostic apparatus 1 includes an ultrasound probe 3 inserted into, for example, a body cavity of a subject 2, an ultrasound observation apparatus 4 according to a first embodiment to which the ultrasound probe 3 is detachably connected and a monitor 5 as an ultrasound image display apparatus configured to display an ultrasound image generated by the ultrasound observation apparatus 4. Note that there may also be a configuration in which the ultrasound observation apparatus 4 includes the monitor 5. The ultrasound probe 3 is not limited to one inserted into the subject 2 but may also be an extracorporeal ultrasound probe configured to be attached to the body surface of the subject 2 to acquire acoustic information on an interior of the subject 2.

The ultrasound probe 3 includes an elongated insertion portion 6, a grasping portion 7 provided at a rear end of the insertion portion 6 and a cable 8 that extends from the grasping portion 7, and a connector 9 at an end of the cable 8 is detachably connected to the ultrasound observation apparatus 4. A plurality of (e.g., M) ultrasound vibration elements 12a are arranged along a convex surface provided on a distal end portion 11 of the insertion portion 6, thus providing an ultrasound transducer 12. The plurality of ultrasound vibration elements 12a that constitute the ultrasound transducer 12 are connected to a transmission/reception switching section 21 in the ultrasound observation apparatus 4 via a signal cable 13 so that a plurality of (N that satisfies N<M) neighboring ultrasound vibration elements via a multiplexer which is not shown are sequentially selected.

The ultrasound observation apparatus 4 includes a transmitting section 22 configured to generate a transmission signal, apply the generated transmission signal to the plurality of ultrasound vibration elements 12a and transmit ultrasound and a receiving section 23 configured to receive ultrasound by the plurality of ultrasound vibration elements 12a and amplify the received signal converted to an electric signal. The transmission/reception switching section 21 connects the transmitting section 22 to the signal cable 13 for a transmission period during which the transmitting section 22 transmits a transmission signal and connects the receiving section 23 to the signal cable 13 for a reception period after the transmission period.

The transmitting section 22 includes a transmission waveform generation section 22a configured to generate a transmission signal of a pulsed transmission waveform and a transmission delay section 22b configured to delay the transmission signal of a transmission waveform generated by the transmission waveform generation section, and transmission signals of different phases delayed by the transmission delay section 22b are applied to the above-described plurality of ultrasound vibration elements 12a via the transmission/reception switching section 21.

With the application of transmission signals of different phases applied to the plurality of ultrasound vibration elements 12a, ultrasound beams transmitted from the plurality of ultrasound vibration elements 12a are caused to converge into a lens shape and propagate through the inside of the subject 2.

Ultrasound reflected by a part inside the subject 2 where an acoustic impedance changes is received by the plurality of ultrasound vibration elements 12a used for transmission, converted to an electric signal which becomes an ultrasound received signal (simply abbreviated as a "received signal"), inputted to the receiving section 23, and the receiving section 23 performs reception processing such as amplification.

The ultrasound observation apparatus 4 includes a phasing addition section 24 configured to perform phasing addition on the received signals of the plurality of ultrasound vibration elements 12a outputted from the receiving section 23, a signal processing section 25 configured to perform signal processing such as gain correction, logarithmic compression, detection and contour emphasis, and an image generation section 26 configured to perform image processing on an output signal of the signal processing section 25 by appropriately setting image quality and generating an image signal.

Furthermore, the ultrasound observation apparatus 4 includes a measuring section 27 configured to measure predetermined measuring items related to administration of a contrast medium on a signal of the image generation section 26 (or an output signal of the signal processing section 25), an image quality setting changing section 28 configured to change an image quality setting of the image generation section 26 and a control section 29 configured to control the change of the image quality setting of the image quality setting changing section 28 based on the measurement result by the measuring section 27.

Furthermore, the ultrasound observation apparatus 4 includes an input section (or input apparatus) 31 configured of a keyboard or the like to instruct to start administration (or start injection) of a contrast medium and a recording section (or recording apparatus) 32 configured to record TIC analysis data for analyzing a luminance change curve (time intensity curve: hereinafter abbreviated as "TIC") of image data in the target region to be observed from the start of administration of the contrast medium with the same image quality setting (first image quality setting) as that at the start of administration of the contrast medium.

The above-described image generation section 26 includes an image quality setting section (or image quality setting circuit) 26a configured to be settable to a first image quality setting which is an appropriate or optimum image quality setting in a first observation mode state (or a first observation phase) when observing how the contrast medium flows into a target region as a contrast imaging mode in the case of the starting of administration of the contrast medium, and a second image quality setting which is an appropriate or optimum image quality setting in a second observation mode state (or a second observation phase) when observing how the contrast medium is connected when the first observation mode state is changed to a state in which the contrast medium is retained in a target region and the contrast medium is retained (also referred to as a predetermined retention state), and a coordinate transformation section (or coordinate transformation circuit) 26b configured to perform coordinate transformation on an image signal with image quality set by the image quality setting section 26a.

The image signal coordinate-transformed by the coordinate transformation section 26b is outputted to the monitor 5 and an ultrasound image of the target region is displayed on a display surface of the monitor 5.

The measuring section 27 includes a luminance analysis section (or luminance analysis circuit) 27a configured to analyze or measure a luminance value of the image signal of, for example, the image quality setting section 26a of the image generation section 26. Note that the measuring section 27 includes a time measuring section (or time measuring circuit) 27b configured to measure time for calculating timing of changing an image quality setting through only time measurement without using the luminance analysis section 27a when a method for calculating timing of changing an image quality setting through time measurement is selected from the input section 31 as will be described later. In other words, the measuring section 27 measures the above-described luminance value or time as the above-described predetermined measurement items related to administration of the contrast medium.

The luminance analysis section 27a measures or analyzes at least one of an average value of a luminance value (also called "luminance average value") of an image signal (or image data) in a target region specified or set by, for example, the input section 31, a maximum value of the luminance value, a variance value of the luminance value and a change rate of the luminance value. In other words, in the luminance value as a predetermined measurement item, an average value and a variance value or the like constitute further subdivided measurement items.

The luminance analysis section 27a outputs the measurement result or analysis result to the control section 29. The control section 29 includes a timing calculation section (or timing analysis section) 29a configured to calculate or analyze timing at which the state of the contrast medium changes from arrival to retention in the target region based on the measurement result of the luminance analysis section 27a, that is, the luminance value measured by the luminance analysis section 27a.

That is, the timing calculation section (or timing calculation circuit) 29a calculates timing at which a first observation mode state at the start of administration of the contrast medium is changed to a second observation mode state in which the contrast medium is retained in a target region as timing of changing the image quality setting from a first image quality setting state as an appropriate image quality setting in the first observation mode state to a second image quality setting state as an appropriate image quality setting in the second observation mode state.

The control section 29 sends the calculated timing to the image quality setting changing section 28 and controls the image quality setting changing section 28 so as to change the image quality setting section 26a of the image generation section 26 from the first image quality setting state to the second image quality setting state.

The input section 31 includes an administration start instruction section 31a configured to instruct to start administration of the contrast medium, a target region specification section 31b configured to specify a target region, a flash instruction section 31c configured to instruct a manual flash (transmission or radiation of high intensity ultrasound with a high acoustic pressure) and a calculation setting section 31d configured to select or set one from among a plurality of calculation methods (or calculation modes) for calculating timing of changing the image quality setting. Note that the administration start instruction section 31a, the target region specification section 31b, the flash instruction section 31c and the calculation setting section 31d generate corresponding instruction signals or the like through specific key operations on, for example, a keyboard making up the input section 31.

When the calculation method for calculating timing of changing the image quality setting by the calculation setting section 31d is not selected (set), time measurement by the time measuring section 27b and measurement (analysis) of a luminance value by the luminance analysis section 27a may be interlocked with each other according to the presence or absence of an instruction to start administration by the administration start instruction section 31a as follows.

When a user such as an operator instructs to start administration of the contrast medium from the administration start instruction section 31a, the time measuring section 27b of the measuring section 27 measures an elapsed time period (time passage) from the instruction to start administration of the contrast medium as a starting point and measures timing of changing the image quality setting. Note that when the starting of administration of the contrast medium is instructed, a target region may be specified from the target region specification section 31b.

When the calculation method by the luminance analysis section 27a is selected as the method for calculating timing of changing the image quality setting, the luminance analysis section 27a starts measuring a luminance value on an image signal of the target region and measures timing of changing the image quality setting. Furthermore, upon receiving a signal for specifying the target region from the input section 31, the image quality setting changing section 28 sets the image quality setting section 26a of the image generation section 26 to a first image quality setting state.

When the flash instruction section 31c instructs a manual flash, the control section 29 controls the transmitting section 22 so as to raise an output level from a normal output level of a transmission signal to a flash output level which is a higher output level and bubbles of the contrast medium are destroyed by being irradiated with ultrasound with a higher acoustic pressure. When a set time period elapses, the control section 29 controls the transmitting section 22 so as to restore the output level of the normal transmission signal.

When the calculation method is set from the calculation setting section 31d, the measuring section 27 and the control section 29 calculate timing of changing the image quality setting according to the set calculation method.

In a contrast imaging mode in which administration of the contrast medium is started, the above-described recording section 32 records a chronological luminance value from the initial state as TIC analysis data with the same image quality setting state. In contrast, an image signal outputted to the monitor 5 is set to the first image quality setting state and the second image quality setting state appropriate to the first observation mode state and the second observation mode state respectively.

Figure 2A:
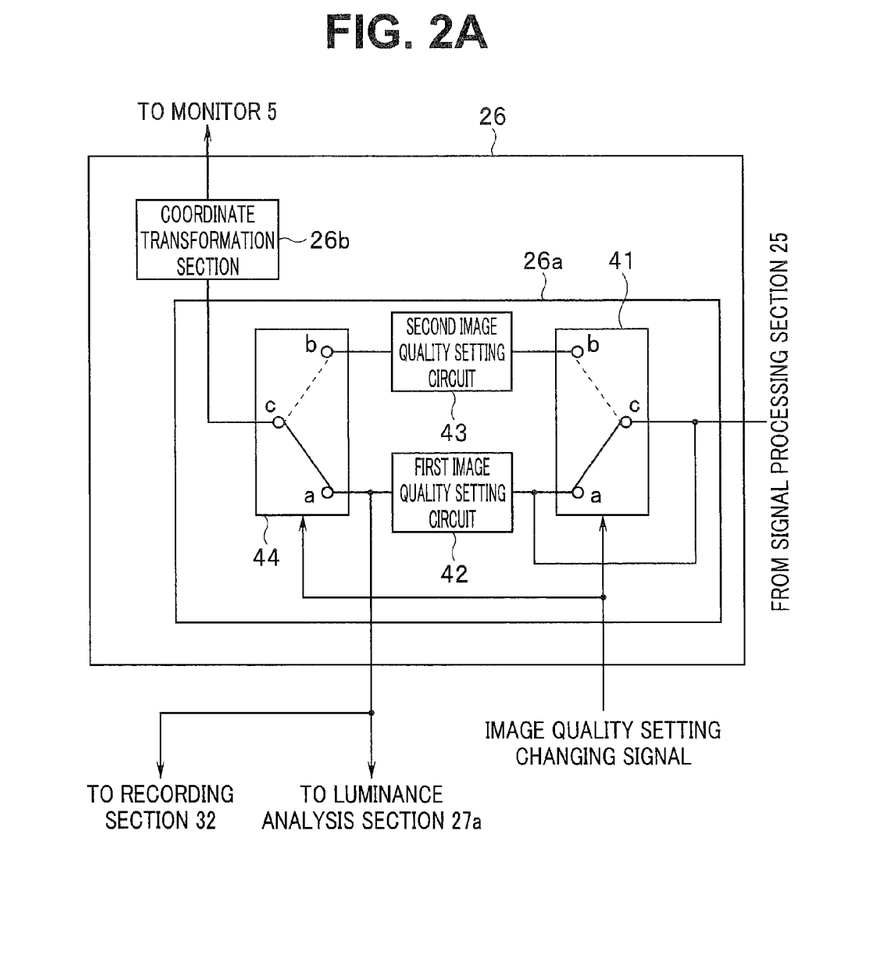
FIG. 2A is a diagram illustrating a configuration of an image quality setting section.

FIG. 2A illustrates one configuration example of the image quality setting section 26a. An image signal from the signal processing section 25 is inputted to a common contact c of a first changeover switch 41 that constitutes the image quality setting section 26a and is also inputted to a first image quality setting circuit 42 configured to set image quality of the image signal to first image quality. Contacts a and b of the first changeover switch 41 are respectively connected to respective input ends of the first image quality setting circuit 42 and a second image quality setting circuit 43 configured to set image quality of the image signal to second image quality. Respective output ends of the first image quality setting circuit 42 and the second image quality setting circuit 43 are respectively connected to contacts a and b of the second changeover switch 44 and a common contact c is connected to an input end of the coordinate transformation section 26b and an output end of the coordinate transformation section 26b is connected to an input end of the monitor 5. The first changeover switch 41 and the second changeover switch 44 are changed as being interlocked with each other by an image quality setting changeover signal outputted from the image quality setting changing section 28. Note that the image quality setting changing section 28 outputs the image quality setting changeover signal under the control of the control section 29.

For example, the first changeover switch 41 and the second changeover switch 44 are changed by an image quality setting changeover signal in such a way that each common contact c is electrically continuous to each contact a in the first observation mode state in which administration of the contrast medium is started as shown by a solid line and each common contact c is electrically continuous to each contact b in a second observation mode state for observing how the contrast medium is retained as shown by a dotted line.

Furthermore, the output end of the first image quality setting circuit 42 is connected to the recording section 32 and connected to the luminance analysis section 27a as well.

With such a configuration, the recording section 32 records an image signal in the first image quality setting state by the first image quality setting circuit 42. Furthermore, the luminance analysis section 27a analyzes a luminance value of the image signal in the first image quality setting state.

Figure 2B:
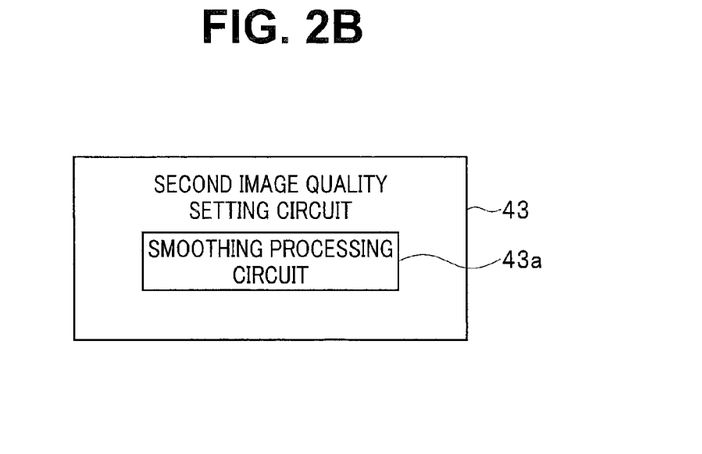
FIG. 2B is a diagram illustrating a second image quality setting circuit provided with a smoothing processing circuit.

As shown in FIG. 2B, the second image quality setting circuit 43 is provided with a smoothing processing circuit 43a which is constructed of, for example, a median filter or a low-pass filter configured to perform smoothing processing, for which a higher smoothing processing level is set than for the smoothing processing circuit provided for the first image quality setting circuit 42. Alternatively, the function of the smoothing processing circuit is turned OFF in the first image quality setting circuit 42 and the second image quality setting by the second image quality setting circuit 43 satisfies a condition under which a higher smoothing processing level is set than the first image quality setting by the first image quality setting circuit 42.

Note that instead of the smoothing processing circuit 43a, the second image quality setting circuit 43 may be configured to perform processing that satisfies a condition under which the second image quality setting has a higher frame correlation value than the first image quality setting or has a higher persistence processing level. In other words, compared to the first image quality setting of the first image quality setting circuit 42, the second image quality setting of the second image quality setting circuit 43 satisfies at least one of conditions: having a higher level of smoothing processing, having a higher frame correlation value and having a higher level of persistence processing.

Note that FIG. 1 illustrates one configuration example and the configuration in FIG. 1 may be changed. For example, in FIG. 1, although the control section 29 and the measuring section 27 are shown as different blocks, the control section 29 may be configured to include the function of the measuring section 27, for example. In FIG. 1, although the image quality setting changing section 28 and the image generation section 26 are shown as different blocks, the image generation section 26 may be configured to include the function of the image quality setting changing section 28, for example, and the image quality setting changing section 28 in the image generation section 26 may be configured to change the image quality setting of the image quality setting section 26a in the image generation section 26 based on a control signal from the control section 29.

Furthermore, in this case, an image quality setting section 26a as shown in FIG. 2A may be disposed in the image quality setting changing section 28 in the image generation section 26 and the image quality setting changing section 28 may be configured to change an image quality setting of the image quality setting section 26a in the image quality setting changing section 28. In addition, although the control section 29 and the image quality setting changing section 28 are shown as different blocks in the configuration of FIG. 1, the control section 29 may be configured to include the function of the image quality setting changing section 28, for example, and the image quality setting changing section 28 in the control section 29 may be configured to change the image quality setting of the image quality setting section 26a in the image generation section 26.

Figure 2C:
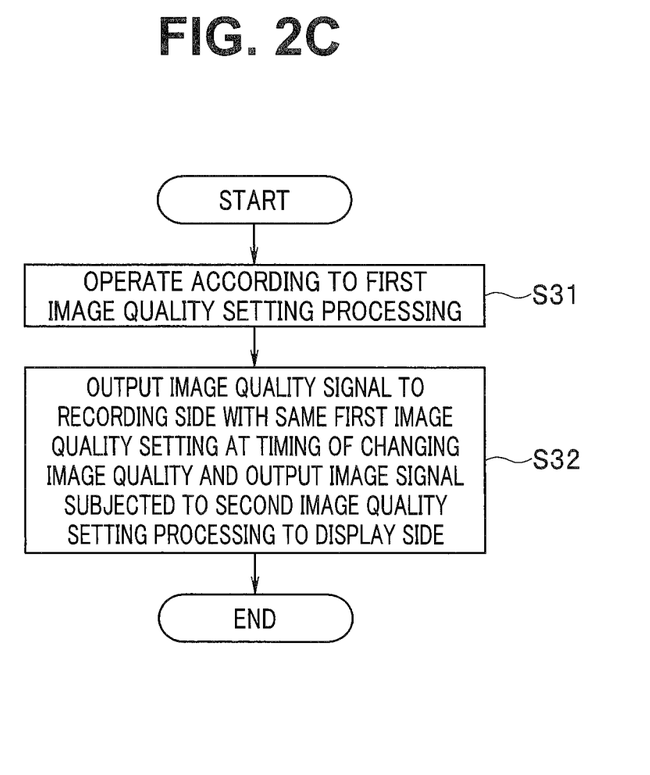
FIG. 2C is a flowchart illustrating a process by the image quality setting section of changing image quality by software.

Note that although FIG. 2A illustrates a configuration in which the image quality setting is changed by hardware, the image quality setting may be changed by software as shown in FIG. 2C. FIG. 2C illustrates processing that operates according to first image quality setting processing first, and changes image quality setting processing at timing of changing the image quality setting (change of image quality).

In first step S31, the image quality setting section 26a operates according to the first image quality setting processing. In this case, an image signal of first image quality generated by the first image quality setting processing is outputted to the display side and the recording side. At timing of changing image quality, as shown in step S32, the image quality setting section 26a outputs the image signal being subjected to the same first image quality setting processing to the recording section 32 side and outputs an image signal of second image quality subjected to the second image quality setting processing to the display side by changing parameter set values and processing contents or the like in the case of the first image quality setting processing.

Note that even when a manual flash is executed, the image quality setting section 26a operates according to the first image quality setting processing at timing at which the manual flash is executed as shown in step S31 and performs the process in step S32 at subsequent timing of changing image quality.

Figure 3:
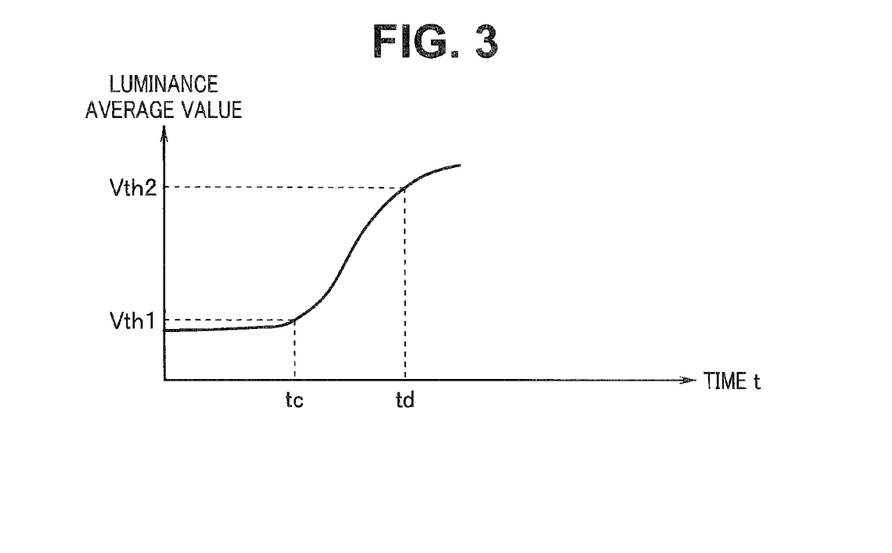
FIG. 3 is a diagram illustrating how luminance analyzed by a luminance analysis section changes.

FIG. 3 illustrates a characteristic example of a luminance change curve (TIC) when analyzed by the luminance analysis section 27a. Based on the analyzed TIC, the luminance analysis section 27a determines that, for example, timing at which the luminance average value as an average value of the luminance value exceeds the level of a threshold $Vth1$ as a predetermined threshold as a time tc of timing at which the contrast medium arrives at the target region. Furthermore, the luminance analysis section 27a determines, for example, timing at which the luminance average value exceeds the level of the threshold $Vth1$ and then further exceeds a threshold $Vth2$ which is higher than the threshold $Vth1$ as a time td of timing at which the contrast medium is retained in the target region.

Instead of an average value of the luminance value, the luminance analysis section 27a may analyze one of a maximum value of the luminance value, a variance value of the luminance value and a change rate of the luminance value, and may determine that timing at which a predetermined threshold is exceeded is the time tc of timing at which the contrast medium arrives at the target region. Then, (the timing calculation section 29a of) the control section 29 controls measurement by the measuring section 27 at the timing (in accordance with the setting of the calculation method by the calculation setting section 31d).

Figure 7:
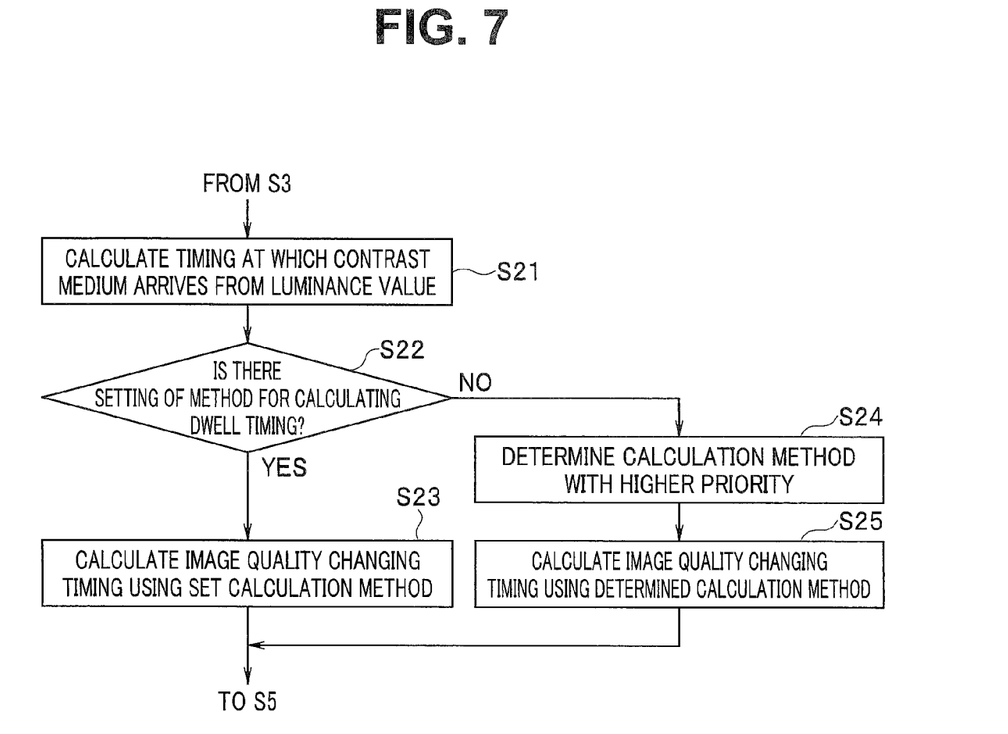
FIG. 7 is a flowchart illustrating a detailed process of step S7 in FIG. 6.

For example, in the case where time measurement (instead of measurement of a luminance value) is set by the calculation setting section 31d, the time td of timing in a predetermined retention state in which the contrast medium is retained in the target region is measured through time measurement from the time tc of the above-described timing. On the other hand, in the case where measurement of a luminance value is set by the calculation setting section 31d, the time td of timing at which the contrast medium is retained in the target region is calculated (measured) through measurement of the luminance value from the time tc of the above-described timing. In the case where the calculation method is not set by the calculation setting section 31d, priority may be set so that the time td of timing at which the contrast medium is retained in the target region is measured through measurement of the luminance value (FIG. 7 illustrates such an operation example).

Note that one of a maximum value of the luminance value, a variance value of the luminance value and a change rate of the luminance value may be analyzed instead of using an average value of the luminance value also in the case where the timing is determined as the time td of timing at which the contrast medium is retained in the target region through measurement of the luminance value.

In other words, (the luminance analysis section 27a of) the measuring section 27 may measure at least one of an average value of the luminance value, a maximum value of the luminance value, a variance value of the luminance value and a change rate of the luminance value, and the control section 29 may control the setting change by the image quality setting changing section 28 by assuming that timing at which at least one of an average value of the luminance value, a maximum value of the luminance value, and a variance value of the luminance value exceeds a predetermined threshold or timing at which the change rate of the luminance value falls below a predetermined threshold as a predetermined retention state in which the contrast medium is retained in the target region.

Figure 4:
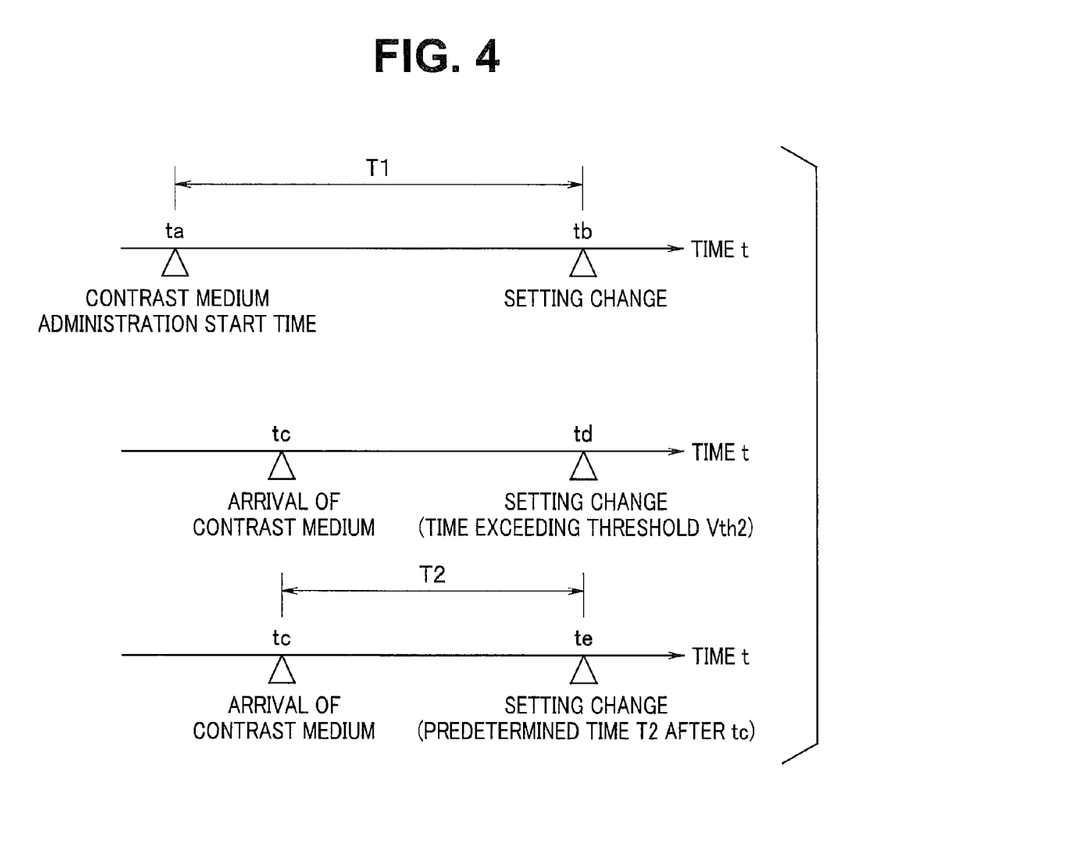
FIG. 4 is a diagram illustrating timing of changing image quality after starting administration of a contrast medium.

FIG. 4 is a diagram illustrating a calculation method for calculating timing of changing an image quality setting.

There are two types of timing of changing an image quality setting in the contrast imaging mode:

(1) timing at which an observation mode state (observation phase) is changed from the start of administration of the contrast medium, and (2) timing at which an observation mode state (observation phase) is changed from execution timing at which a manual flash is executed by the flash instruction section 31c.

In the case of (1), three calculation methods are available as shown in FIG. 4.

(A) As shown on a top row in FIG. 4, the image quality setting is changed by determining a time tb of timing after a predetermined time period T1 measured from a time to of timing of starting administration of the contrast medium as a time at which the setting of a state in which the contrast medium is retained should be changed (time for setting change).

(B) As shown on a middle row in FIG. 4, the image quality setting is changed by the luminance analysis section 27a analyzing luminance of the target region from a time tc of timing at which the contrast medium arrives at the target region and determining, when the analysis result reaches a threshold, that it is the time to change the setting of a state in which the contrast medium is retained. For example, the image quality setting is changed by determining a time td of timing at which an average value of luminance exceeds the threshold Vth2 as a time in a state in which the contrast medium is retained. Note that as described above, the time td of timing at which the image quality setting is changed may be determined by analyzing one of a maximum value of the luminance, a variance value of the luminance and a change rate value of luminance instead of the average value of luminance.

(C) As shown on a lowest row in FIG. 4, the image quality setting is changed by determining that a time to of timing a predetermined time period T2 after the time tc of timing at which the contrast medium arrives at the target region as a time of changing the setting of a state in which the contrast medium is retained.

Figure 5:
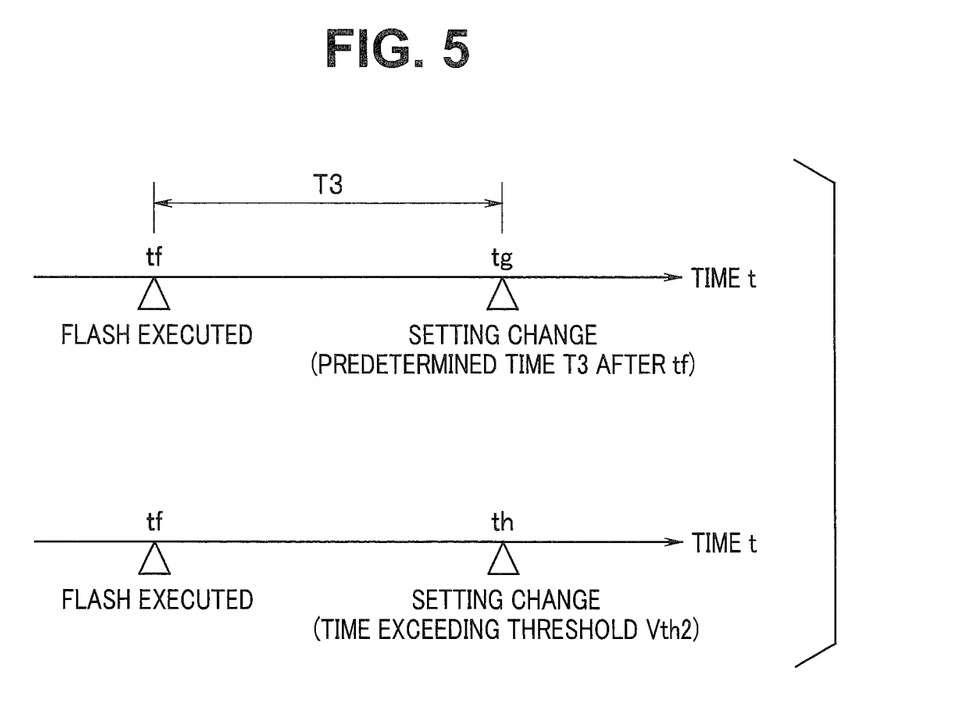
FIG. 5 is a diagram illustrating timing of changing image quality after executing a manual flash.

In the case of (2) above, two calculation methods are available as shown in FIG. 5.

(A) As shown on an upper row in FIG. 5, the image quality setting is changed from a second image quality setting to a first image quality setting at time tf of timing at which a manual flash is executed, and the image quality setting is changed from the first image quality setting to the second image quality setting by determining that a time tg at timing a predetermined time period T3 later is a time of the setting change of a state in which the contrast medium is retained through time measurement.

(B) As shown on a lower row in FIG. 5, after changing the image quality setting from the second image quality setting to the first image quality setting at time tf of timing at which a manual flash is executed, luminance of the target region is analyzed and the image quality setting is changed from the first image quality setting to the second image quality setting by determining according to the analysis result that at a time th of timing at which the luminance value exceeds the threshold Vth2, a state is set in which the contrast medium is retained.

In this case, the luminance analysis section 27a analyzes one of an average value of the luminance, a maximum value of the luminance, a variance value of the luminance and a change rate value of the luminance. Note that in the present Description, the respective sections of the transmission/reception switching section 21, the transmitting section 22, the receiving section 23, the phasing addition section 24, the signal processing section 25, the image generation section 26, the measuring section 27, the image quality setting changing section 28 and the control section 29 have substantially the same meanings as those substituted by their respective circuits. For this reason, for example, the control section 29 may be substituted by a control circuit and the same may also apply to the other sections except the control section 29.

The ultrasound observation apparatus 4 according to the present embodiment is an ultrasound observation apparatus that transmits ultrasound to a subject to which a contrast medium is administered, receives ultrasound reflected by the contrast medium in a target region of the subject and generates an ultrasound image based on an ultrasound signal obtained from the received ultrasound, and includes the measuring section 27 configured to measure predetermined measuring items related to administration of the contrast medium, the image quality setting changing section 28 configured to change an image quality setting of the ultrasound image from one to the other of a first image quality setting suitable for observing how the contrast medium flows into the target region and a second image quality setting suitable for observing how the contrast medium is retained in the target region, and the control section 29 configured to control operation of changing the setting by the image quality setting changing section 28 based on the measurement result of the measuring section 27. The above-described configuration may also be said to be the following configuration.

The ultrasound observation apparatus 4 according to the present embodiment includes the transmitting section 22 configured to transmit ultrasound to a subject to which a contrast medium is administered, the receiving section 23 configured to receive ultrasound reflected by the contrast medium in a target region of the subject, the image generation section 26 configured to generate an ultrasound image based on an ultrasound signal obtained from the received ultrasound, the measuring section 27 configured to measure predetermined measuring items relating to administration of the contrast medium, the image quality setting changing section 28 configured to change an image quality setting of the ultrasound image from one to the other of a first image quality setting suitable for observing how the contrast medium flows into the target region and a second image quality setting suitable for observing how the contrast medium is retained in the target region, and the control section 29 configured to control operation of changing the setting by the image quality setting changing section 28 based on the measurement result of the measuring section 27.

Next, a typical operation of the present embodiment will be described with reference to FIG. 6. An operator inserts the ultrasound probe 3 into the subject 2, causes the distal end portion 11 of the insertion portion 6 to come into contact with an inner wall in the subject 2 and sets the ultrasound probe 3 so as to be able to acquire an ultrasound image. Then, as shown in step S1, the operator sets a contrast imaging mode from the input section 31. In this case, as shown in step S2, the image quality setting changing section 28 sets the image quality setting section 26a to a first image quality setting.

As shown in step S3, the operator administers (injects) the contrast medium into the subject 2.

When the operator wants to calculate timing of changing an image quality setting through time measurement, the operator instructs to start administration of the contrast medium from the administration start instruction section 31a. Then, as shown in step S4, the control section 29 keeps a time to start administration of the contrast medium. The time measuring section 27b measures the time of changing image quality with the instruction to start administration of the contrast medium as a starting point. As described with reference to FIG. 4, when the time tb of timing after the predetermined time period T1 is reached, it is determined that a state is set in which the contrast medium is retained in the target region. As shown in step S5, the time measuring section 27b determines that it is the time to change the setting, sends the determination result to the control section 29, and the control section 29 controls the image quality setting changing section 28 so as to change the image quality setting of the image quality setting section 26a from the first image quality setting to the second image quality setting.

On the other hand, when the operator wants to calculate (or measure) timing of changing the setting according to the luminance after starting administration of the contrast medium, the operator specifies a calculation method using luminance.

In step S6, the luminance analysis section 27a measures (calculates) (an arrival) time tc of timing at which the contrast medium arrives at the target region as shown in, for example, FIG. 3 based on the luminance (as a time of timing at which the average luminance value exceeds the threshold Vth1). The luminance analysis section 27a further measures (calculates) timing of changing the setting in a state in which the contrast medium is retained based on the luminance from the calculated (arrival) time tc.

For example, as shown in FIG. 3, at the time td of timing at which the average luminance value exceeds the threshold Vth2, the luminance analysis section 27a sends the measurement result to the control section 29. Alternatively, a time at timing of changing the setting of the state in which the contrast medium is retained may be measured through time measurement from the time tc by the time measuring section 27b and the measurement result may be sent to the control section 29. After the process in step S6, the flow proceeds to the process in step S5.

As shown in step S5, the control section 29 controls the image quality setting changing section 28 to change the image quality setting of the image quality setting section 26a from the first image quality setting to the second image quality setting.

At a time at timing of changing the setting of the state in which the contrast medium is retained through temporal measurement or measurement using luminance, since the image quality setting changes from the first image quality setting to the second image quality setting as shown in step S5, the operator can perform observation without effort with appropriate image quality, making it easier to grasp in detail how the contrast medium is connected in the target region in the state in which the contrast medium is retained.

After step S5, as shown in step S7, the control section 29 monitors flash execution by a manual flash instruction from the flash instruction section 31c of the input section 31.

Figure 6:
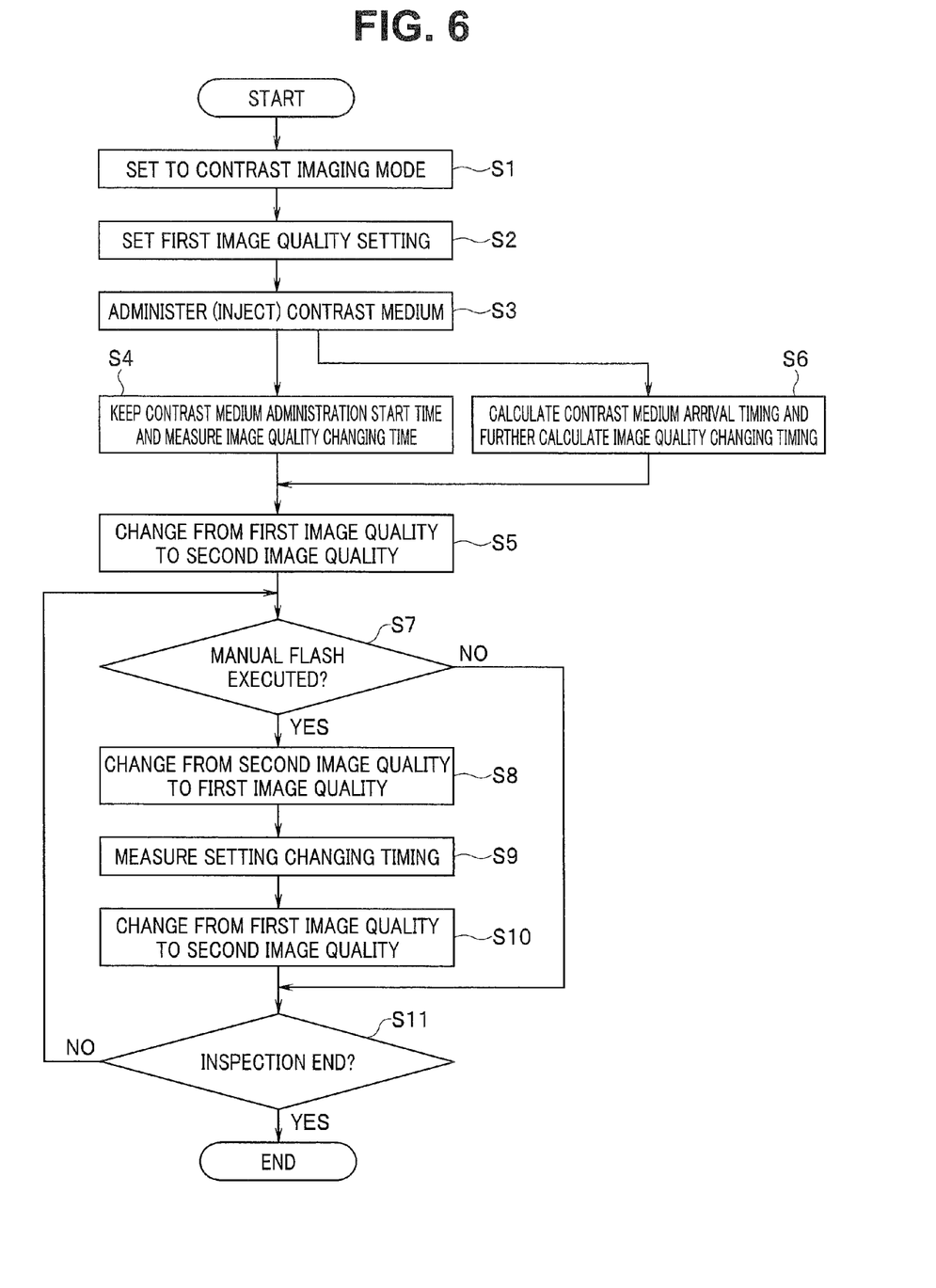
FIG. 6 is a flowchart illustrating processing according to a first embodiment.

When the flash execution is not performed, the flow proceeds to a process in step S11, the control section 29 determines whether or not an instruction to end an inspection is inputted from the input section 31, ends the process in FIG. 6 when an instruction to end an inspection is inputted or returns to the process in step S7 when no instruction to end an inspection is inputted.

On the other hand, when flash execution is performed in the determination process in step S7, the flow proceeds to a process in step S8, and in step S8, the image quality setting changing section 28 changes the image quality setting of the image quality setting section 26a from the second image quality setting to the first image quality setting. In next step S9, the measuring section 27 measures the timing of changing the setting using the calculation method shown in FIG. 5 (temporally or through a luminance analysis).

At timing at which it is determined that a state is set in which the contrast medium is retained, the control section 29 controls the image quality setting changing section 28 to change the image quality of the image quality setting section 26a from the first image quality setting to the second image quality setting as shown in step S10. In the present embodiment, since image quality of the image quality setting section 26a is changed from the first image quality setting to the second image quality setting at timing at which it is determined that a state is set in which the contrast medium is retained in this way, the operator can observe without effort how the contrast medium flows into the target region in detail with appropriate image quality and easy to grasp. After the process in step S10, the flow proceeds to the process in aforementioned step S11.

FIG. 7 illustrates details of the process in S6. When the calculation method using luminance is specified or selected in step S3, the luminance analysis section 27a calculates the time tc of timing at which the contrast medium arrives at the target region through measurement of the luminance value as shown in step S21 and sends the calculation result to the control section 29.

In next step S22, the control section 29 determines whether or not the calculation setting section 31d sets a selection of a calculation method for calculating timing at which the contrast medium is retained in the target region from the time tc of timing at which the contrast medium arrives at the target region (in other words, timing at which the image quality setting is changed) through a calculation using the luminance value or a calculation through time measurement.

In the case of a determination result where the calculation method is set, in next step S23, the measuring section 27 calculates timing at which the contrast medium is retained in the target region or timing of changing the image quality using the set calculation method. When the measuring section 27 calculates the timing at which the contrast medium is retained in the target region, the measuring section 27 sends the calculation result to the control section 29 and the control section 29 performs control as shown in step S6.

On the other hand, in the case of a determination result in step S22 showing that the calculation method is not set, the control section 29 determines in step S24 to adopt the calculation method for which high priority is set.

When the user calculates timing at which the contrast medium is retained in the target region, if the user wants to use one of a luminance value and a time with higher priority than the other in advance, the user inputs information on the priority the user wants from the input section 31 and the inputted information on the priority is stored in a memory or the like that forms a priority information storage section in the control section 29 or the measuring section 27. In step S24, the control section 29 adopts a calculation method with higher priority with reference to the information on the priority stored in the memory or the like.

In next step S25, the control section 29 controls the measuring section 27 so as to adopt the calculation method with higher priority to calculate timing at which the contrast medium is retained in the target region or timing of changing the image quality. The measuring section 27 adopts the calculation method with higher priority and calculates timing at which the contrast medium is retained in the target region or timing of changing the image quality.

After calculating timing at which the contrast medium is retained in the target region, the measuring section 27 sends the calculation result to the control section 29 and the control section 29 performs control as shown in step S6.

According to the present embodiment that operates in this way, it is possible to observe how the contrast medium flows into the target region and how the contrast medium is retained with an appropriate image quality setting respectively.

Furthermore, by giving an instruction to start administration of the contrast medium, the time measuring section 27b can calculate timing of changing image quality setting through time measurement, automatically change the image quality setting from the first image quality setting to the second image quality setting, and thereby save time and effort of changeover by the user.

It is also possible to calculate timing of changing the image quality setting based on a luminance value by the luminance analysis section 27a.

What is claimed is:

1. An ultrasound observation apparatus comprising:
a processor comprising hardware, wherein the processor is configured to:
generate an ultrasound image based on an ultrasound signal obtained from received ultrasound reflected by contrast medium in a target region of a subject;
perform a measuring process to measure predetermined measuring items related to administration of the contrast medium, and generate measurement results based on results of the measuring process;
perform a setting changing operation to change an image quality setting of the ultrasound image from one to another of a first image quality setting suitable for observing how the contrast medium flows into the target region and a second image quality setting suitable for observing how the contrast medium is retained in the target region; and
control the setting changing operation based on the measurement results.

2. The ultrasound observation apparatus according to claim 1,
wherein the processor is configured to control the setting changing operation based on:
a measurement result based on a luminance value of the ultrasound image in the target region: or
a measurement result based on time measurement related to administration of the contrast medium.

3. The ultrasound observation apparatus according to claim 1,
wherein compared to the first image quality setting, the second image quality setting satisfies at least one of conditions of having a higher level of smoothing processing, a higher frame correlation value and a higher level of persistence processing.

4. The ultrasound observation apparatus according to claim 3,
wherein the processor is configured to:
measure a luminance value of the ultrasound image in the target region;
analyze a retention state of the contrast medium in the target region based on the luminance value measured: and
control the setting changing operation so as to change the image quality setting when a predetermined retention state is set.

5. The ultrasound observation apparatus according to claim 4,
wherein the processor is configured to:
perform the measuring process to measure at least one of an average value of the luminance value, a maximum value of the luminance value, a variance value of the luminance value and a change rate of the luminance value; and
control the setting changing operation assuming that timing at which at least one of the average value of the luminance value, the maximum value of the luminance value and the variance value of the luminance value exceeds a predetermined threshold or timing at which the change rate of the luminance value falls below a predetermined threshold corresponds to the predetermined retention state.

6. The ultrasound observation apparatus according to claim 3,
wherein the processor is configured to:
measure a luminance value of the ultrasound image in the target region; and
determine arriving timing at which the contrast medium arrives at the target region based on the luminance value measured; and
control the setting changing operation to change the image quality setting when a predetermined time period elapses after the contrast medium arrives at the target region.

7. The ultrasound observation apparatus according to claim 6,
wherein the processor is configured to:
perform the measuring process to measure at least one of an average value of the luminance value, a maximum value of the luminance value, a variance value of the luminance value and a change rate of the luminance value; and
control the setting changing operation assuming timing at which at least one of the average value of the luminance value, the maximum value of the luminance value, the variance value of the luminance value and the change rate of the luminance value exceeds a predetermined threshold as the arriving timing of the contrast medium.

8. The ultrasound observation apparatus according to claim 7,
wherein the processor is configured to control a display apparatus to display the ultrasound image at the image quality setting set by the setting changing operation.

9. The ultrasound observation apparatus according to claim 7,
wherein the processor is configured to set the image quality setting of the ultrasound image by changing processing contents of the first image quality setting and the second image quality setting.

10. The ultrasound observation apparatus according to claim 3,
wherein the processor is configured to:
receive an instruction to start administration of the contrast medium;
measure an elapsed time period from a time of receiving the instruction to start administration as a starting time point; and
control the setting changing operation to change the image quality setting based on the elapsed time period measured.

11. The ultrasound observation apparatus according to claim 3,
wherein the processor is configured to control, when a manual flash is instructed by a flash instruction, the setting changing operation so that the image quality setting becomes the first image quality setting in conjunction with execution of a flash that transmits ultrasound with high intensity in response to the flash instruction.

12. The ultrasound observation apparatus according to claim 11,
wherein after changing the image quality setting to the first image quality setting in conjunction with the execution of the flash that transmits the ultrasound with the high intensity, the processor is configured to change the image quality setting from the first image quality setting to the second image quality setting based on the measurement results generated.

13. The ultrasound observation apparatus according to claim 3,
wherein the processor is further configured to control a memory to record video data with the first image quality setting as luminance change curve analysis data independently of the setting changing operation performed.

14. The ultrasound observation apparatus according to claim 1,
wherein the processor is configured to:
control a memory to store priority information regarding priority given to one of:
calculating retention timing at which the contrast medium is retained in the target region from arrival timing at which the contrast medium arrives at the target region through measurement based on a luminance value of the ultrasound image in the target region as one of the predetermined measuring items; and
calculating the retention timing from the arrival timing through time measurement from the arrival timing; and
calculate the retention timing with reference to the priority information stored in the memory.

* * * * *